US010078150B2

(12) United States Patent
Deinert et al.

(10) Patent No.: US 10,078,150 B2
(45) Date of Patent: Sep. 18, 2018

(54) DETECTING AND QUANTIFYING MATERIALS IN CONTAINERS UTILIZING AN INVERSE ALGORITHM WITH ADAPTIVE REGULARIZATION

(71) Applicant: Board of Regents, The University of Texas System, Austin, TX (US)

(72) Inventors: Mark Deinert, Golden, CO (US); Andrew J. Gilbert, Richland, WA (US); Benjamin S. McDonald, Richland, WA (US); Sean M. Robinson, Richland, WA (US); Ken D. Jarman, Richland, WA (US); Tim A. White, Richland, WA (US)

(*) Notice: Subject to any disclaimer, the term of this patent is extended or adjusted under 35 U.S.C. 154(b) by 209 days.

(21) Appl. No.: 15/093,525

(22) Filed: Apr. 7, 2016

(65) Prior Publication Data
US 2016/0306068 A1    Oct. 20, 2016

Related U.S. Application Data

(60) Provisional application No. 62/147,194, filed on Apr. 14, 2015.

(51) Int. Cl.
*G01N 23/06* (2018.01)
*G01V 5/00* (2006.01)
(Continued)

(52) U.S. Cl.
CPC ......... *G01V 5/0016* (2013.01); *G01N 23/083* (2013.01); *G01N 23/10* (2013.01)

(58) Field of Classification Search
CPC .... G01V 5/0016; G01N 23/10; G01N 23/083; G01N 23/04
See application file for complete search history.

(56) References Cited

U.S. PATENT DOCUMENTS 6,507,633 B1   1/2003  Elbakri et al.
6,614,874 B2   9/2003  Avinash
(Continued)

FOREIGN PATENT DOCUMENTS

WO    2011037344 A2    3/2011

OTHER PUBLICATIONS

Gilbert et al. "Non-invasive material discrimination using spectral X-ray radiography" (2014) Journal of Applied Physics 115 pp. 154901-1-154901-5.*

(Continued)

*Primary Examiner* — Courtney Thomas

(57) ABSTRACT

A method, system and computer program product for automatically detecting and quantifying materials in containers (e.g., luggage, storage containers, equipment or componentry for processing or handling). An X-ray radiograph of a container is generated. A set of materials of interest (e.g., plutonium, steel) is selected to determine if the object comprises or contains materials of interest. An estimate of the areal densities or thicknesses of each of the selected materials of interest is obtained by minimizing an objective function with respect to the areal densities or thicknesses for each of the selected materials of interest. Adaptive regularization is implemented in the objective function to improve optimization results by adding a constraint to the objective function, where the constraint penalizes the objective function for solutions that do not line up with a prior belief about the solution form (e.g., the solution should not be negative or especially noisy).

22 Claims, 7 Drawing Sheets

(51) Int. Cl.
  *G01N 23/10*   (2018.01)
  *G01N 23/083*   (2018.01)

(56) References Cited

U.S. PATENT DOCUMENTS

| | | |
|---|---|---|
| 2003/0156684 A1 | 8/2003 | Fessler |
| 2009/0052762 A1 | 2/2009 | Dugan et al. |
| 2009/0147919 A1 | 6/2009 | Goto et al. |
| 2010/0232669 A1 | 9/2010 | Ziegler et al. |
| 2011/0075800 A1* | 3/2011 | Bjorkholm ........... G01N 23/087 378/53 |
| 2012/0170826 A1 | 7/2012 | Jang et al. |

OTHER PUBLICATIONS

Gilbert et al., "Non-Invasive Material Discrimination Using Spectral X-Ray Radiography," Journal of Applied Physics, vol. 115, Issue 15, 2014, pp. 154901-1 to 154901-5.

Gilbert et al., "Material Discrimination for Treaty Verification with Multi-Energy, X-Ray Radiography," INMM Annual Meeting 2013 Conference Proceedings, Palm Desert, CA, 2013, pp. 1-7.

Gilbert et al., "Integration of X-Ray and Neutron Radiography Data for Enhanced Discrimination of Materials with High Atomic Number," poster presented at the 2014 Symposium on Radiation Measurements and Applications, Jun. 2014, one page.

* cited by examiner

DETECTING AND QUANTIFYING MATERIALS IN CONTAINERS UTILIZING AN INVERSE ALGORITHM WITH ADAPTIVE REGULARIZATION

CROSS REFERENCE TO RELATED APPLICATIONS

This application is related to the following commonly owned U.S. Patent Application:

Provisional Application Ser. No. 62/147,194, "Detecting and Quantifying Materials in Containers Utilizing an Inverse Algorithm with Adaptive Regularization," filed Apr. 14, 2015, and claims the benefit of its earlier filing date under 35 U.S.C. § 119(e).

GOVERNMENT INTERESTS

This invention was made with government support under Grant No. DE-AC05-76RLO1830 awarded by the U.S. Department of Energy. The U.S. government has certain rights in the invention.

TECHNICAL FIELD

The present invention relates generally to x-ray scanning for detection and quantification of materials in containers (e.g., luggage, storage containers, equipment or componentry for processing or handling) or reprocessing systems or effluents, utilizing an inverse algorithm with adaptive regularization. More particularly the present invention relates to the automatic detection and quantification of materials of interest, including nuclear materials, in luggage, storage containers, and processing or handling systems.

BACKGROUND

Using spectral information to aid in quantitative X-ray radiography has been widely applied since dual-energy body scans were introduced to help distinguish between bone and tissue. More recently, dual-energy radiography has been used in security inspections in an attempt to detect drugs, explosives, and high-atomic-numbered (high-Z) materials. However, a key limitation with the dual-energy technique is that it can only determine two unknowns. These scans are typically done with only two X-ray spectra since models for the components of the X-ray attenuation coefficients are calculated as functions of only density and atomic number. Dual-energy radiography can be used to determine an average density and atomic number (Z) for a given X-ray pathlength between the source and detector plane. This is a significant limiting factor for detection of nuclear materials because higher-Z materials can be shielded by lower-Z materials so that the average Z is below some threshold.

Hence, there is not currently a means for effective and automatic detection of materials, such as dense, high-Z nuclear materials, utilizing X-ray radiography, especially in multi-layered object configurations.

SUMMARY

In one embodiment of the present invention, a method for automatically detecting or quantifying a presence of a material in a container comprises generating a radiograph from a detector response at a detector array, where the detector array detects a transmitted beam which emerges from an object in a container and where the transmitted beam is a portion of a flux in an X-ray beam that is not attenuated by the object. The method further comprises selecting a set of materials of interest used to determine if the object in the container corresponds to one or more of these materials of interest. The method additionally comprises obtaining, by a processor, estimated areal densities for each of the selected set of materials of interest by minimizing an objective function with respect to the areal densities, or linear attenuation coefficients, for each of the selected set of materials of interest, where the objective function comprises a least-squares misfit of a vector containing observed signals at each pixel of the radiograph and a model of the radiography detector response. The minimizing of the objective function occurs by varying a combination and a quantity for each of the selected set of materials of interest at each pixel of the radiograph model until a minimum of the objective function is found. Furthermore, the method comprises implementing adaptive regularization to the objective function to improve optimization results by adding a constraint to the objective function, where the constraint penalizes the objective function as sums of differences in material compositions for each of the selected set of materials of interest in column and row dimensions at each pixel of the radiograph.

Other forms of the embodiment of the method described above are in a system and in a computer program product.

The foregoing has outlined rather generally the features and technical advantages of one or more embodiments of the present invention in order that the detailed description of the present invention that follows may be better understood. Additional features and advantages of the present invention will be described hereinafter which may form the subject of the claims of the present invention.

BRIEF DESCRIPTION OF THE DRAWINGS

A better understanding of the present invention can be obtained when the following detailed description is considered in conjunction with the following drawings, in which.

DETAILED DESCRIPTION

Figure 1:
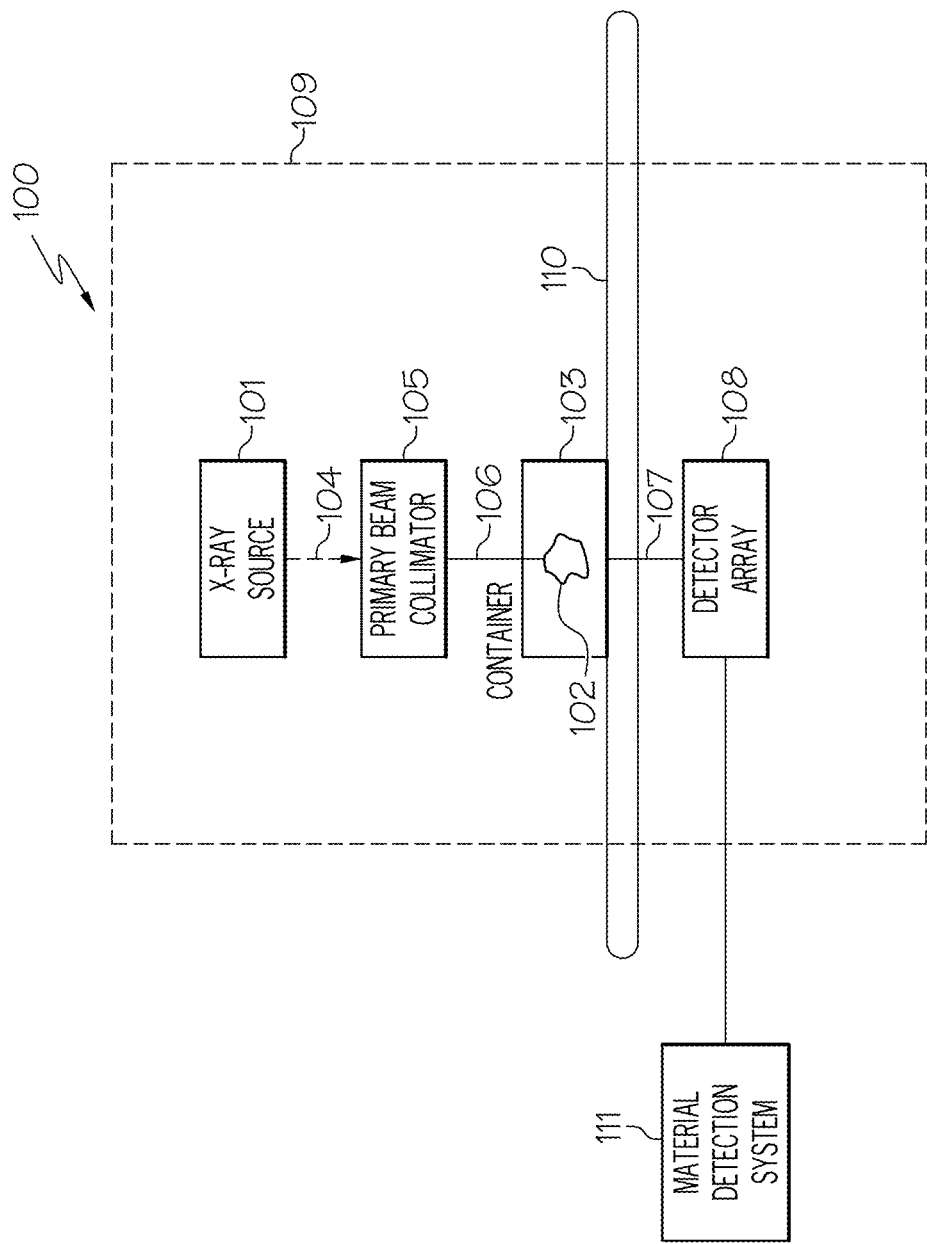
FIG. 1 is an x-ray scanning system for detecting materials in a container in accordance with an embodiment of the present invention.

In the following description, various embodiments are described. For purposes of explanation, specific configurations and details are set forth in order to provide a thorough understanding of the embodiments. It will also be apparent to one skilled in the art that the present invention can be practiced without the specific details described herein. Furthermore, well-known features may be omitted or simplified in order not to obscure the embodiment being described.

While the following discusses the present invention in connection with detecting and quantifying materials, such as dense, high-Z nuclear materials, the principles of the present invention may be applied to detecting the presence or an amount of any material, whether illicit or otherwise, in any type of container, whether cargo, a storage container or a piece of luggage. For example, the principles of the present invention may be applied to ensuring that nuclear fuel pins used in nuclear power plants have the appropriate amount of material (e.g., uranium). In another example, the principles of the present invention may be implemented in a baggage inspection system or a nuclear fuel processing center. Measurement of specific materials in mining, processing, fabrication or handling systems would be other examples. A person of ordinary skill in the art would be capable of applying the principles of the present invention to such implementations. Further, embodiments applying the principles of the present invention to such implementations would fall within the scope of the present invention.

Furthermore, while the following discusses the present invention in connection with utilizing regularization, it is not required in certain embodiments where spectroscopy techniques are used in connection with tomography, such as computerized axial tomography scans. A person of ordinary skill in the art would be capable of applying the principles of the present invention to such implementations. Further, embodiments applying the principles of the present invention to such implementations would fall within the scope of the present invention.

Using spectral information to aid in quantitative X-ray radiography has been widely applied since dual-energy body scans were introduced to help distinguish between bone and tissue. More recently, dual-energy radiography has been used in security inspections in an attempt to detect drugs, explosives, and high-atomic-numbered (high-Z) materials. However, a key limitation with the dual-energy technique is that it can only determine two unknowns. These scans are typically done with only two X-ray spectra since models for the components of the X-ray attenuation coefficients are calculated as functions of only density and atomic number. Dual-energy radiography can be used to determine an average density and atomic number (Z) for a given X-ray pathlength between the source and detector plane. This is a significant limiting factor for detection of nuclear materials because higher-Z materials can be shielded by lower-Z materials so that the average Z is below some threshold. Hence, there is not currently a means for effective and automatic detection of materials, such as dense, high-Z nuclear materials, utilizing X-ray radiography, especially in multi-layered object configurations.

Figure 2:
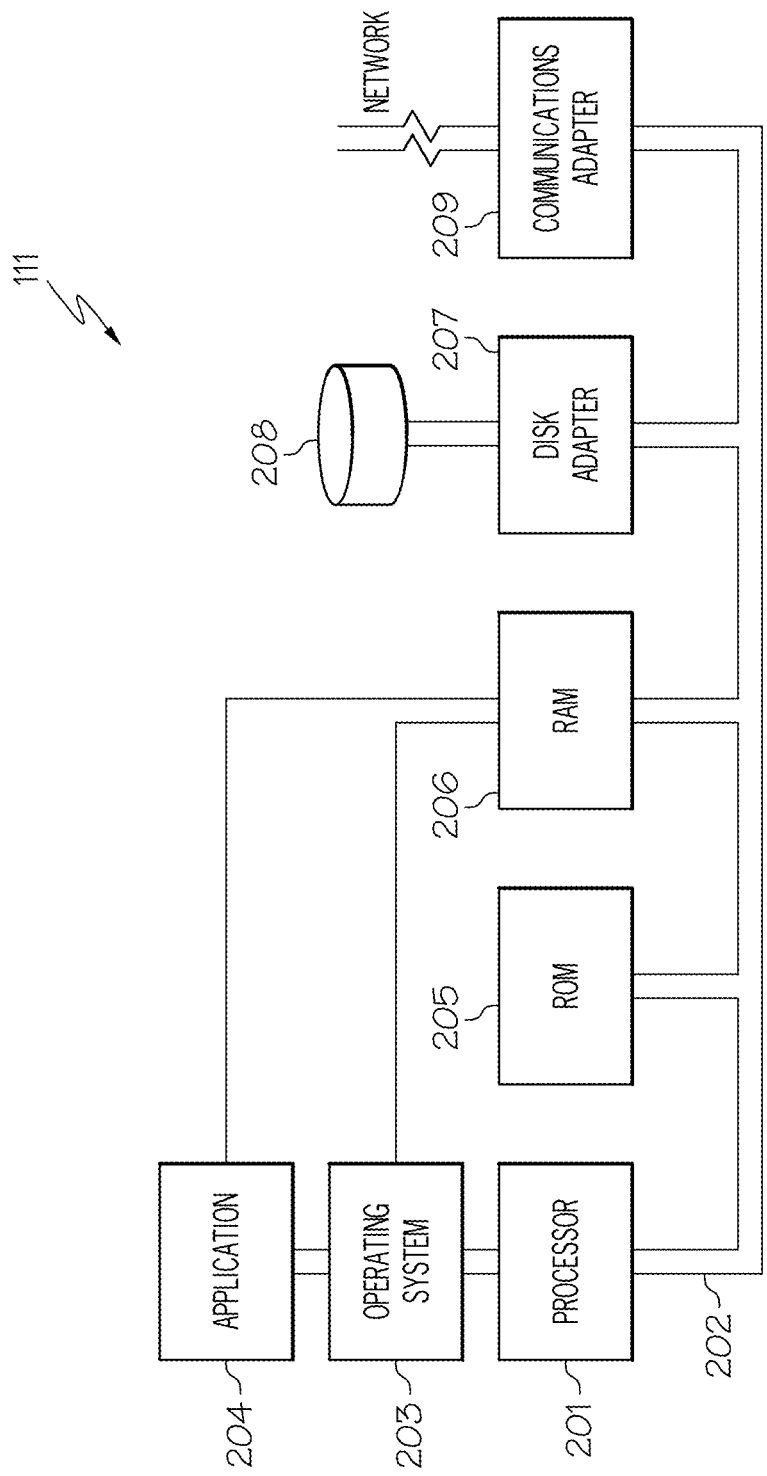
FIG. 2 illustrates a hardware configuration of the material detection system in accordance with an embodiment of the present invention.
Figure 3:
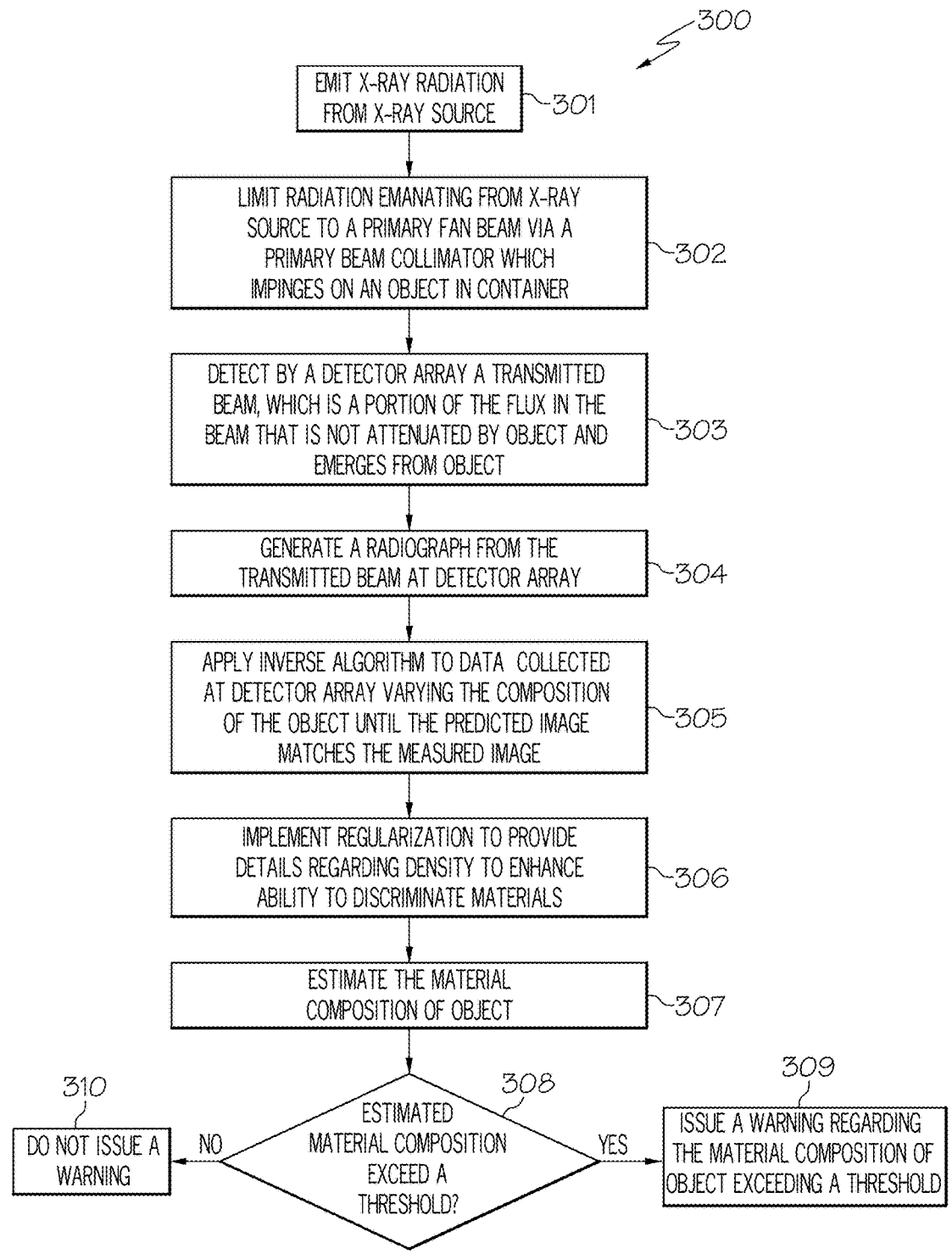
FIG. 3 is a flowchart of a method for detecting a presence and an amount of a material in a container utilizing an inverse algorithm with adaptive regularization in accordance with an embodiment of the present invention.
Figure 4:
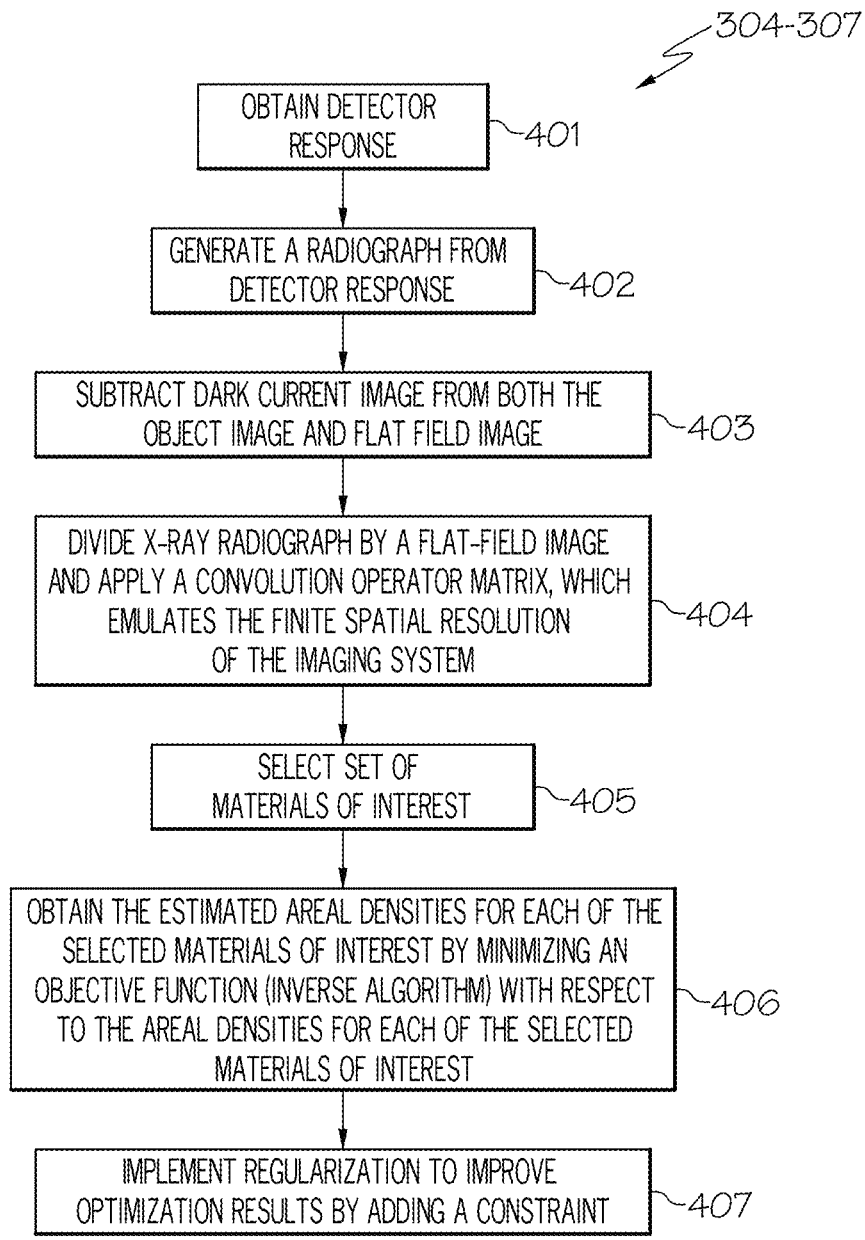
FIG. 4 is a flowchart of a method of the sub-steps of steps 304-307 of FIG. 3 in accordance with an embodiment of the present invention.
Figure 5A:
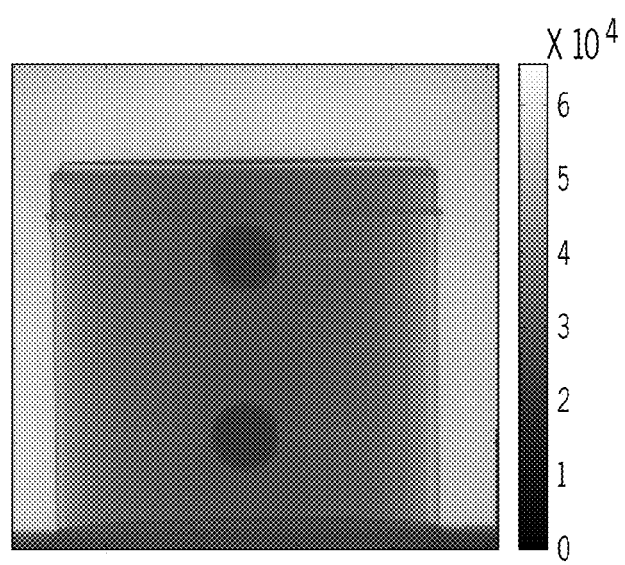
FIG. 5A illustrates the radiographic image of the original X-ray transmission image of the scale AT400R model for the 300 keV endpoint energy in accordance with an embodiment of the present invention.
Figure 5B:
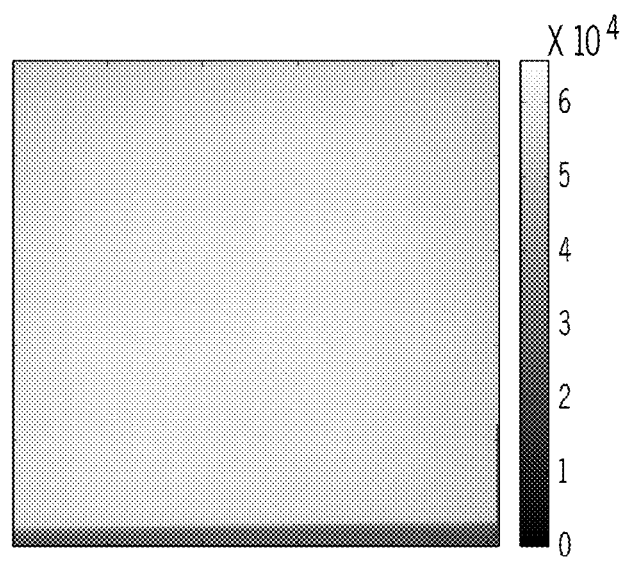
FIG. 5B illustrates the flat field image without the inspected object present in accordance with an embodiment of the present invention.
Figure 5C:
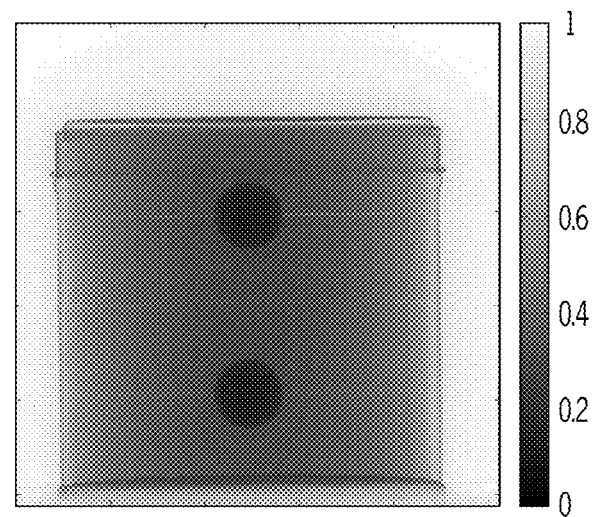
FIG. 5C illustrates the result of the division of the transmission image by the flat field image after the dark image is subtracted from both in accordance with an embodiment of the present invention.
Figure 6A:
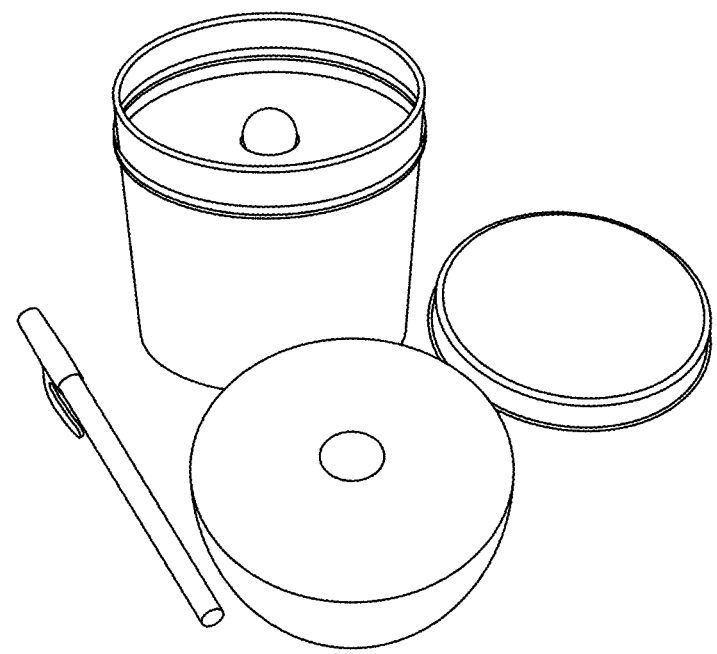
FIG. 6A illustrates the scale-model object used in the inspections in accordance with an embodiment of the present invention.
Figure 6B:
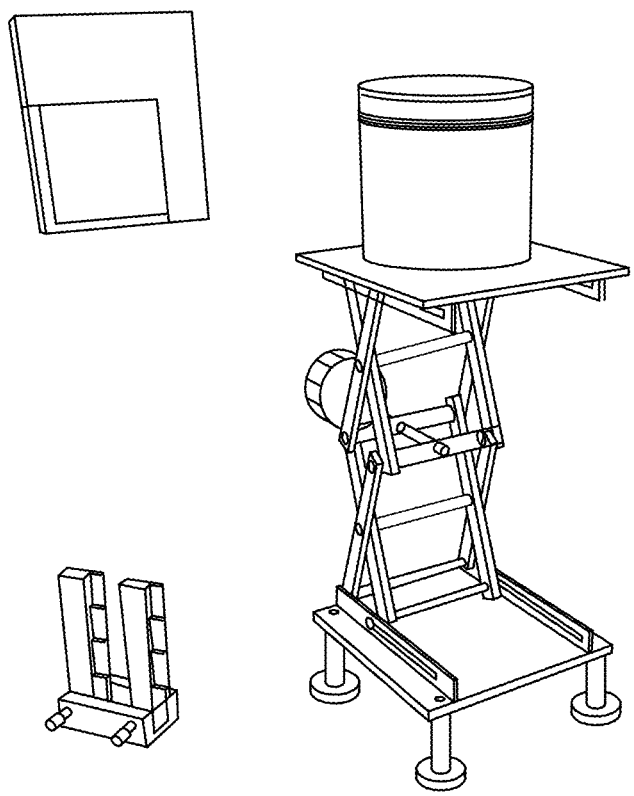
FIG. 6B shows the experimental setup and detector in accordance with an embodiment of the present invention.
Figures 7A, 7B:
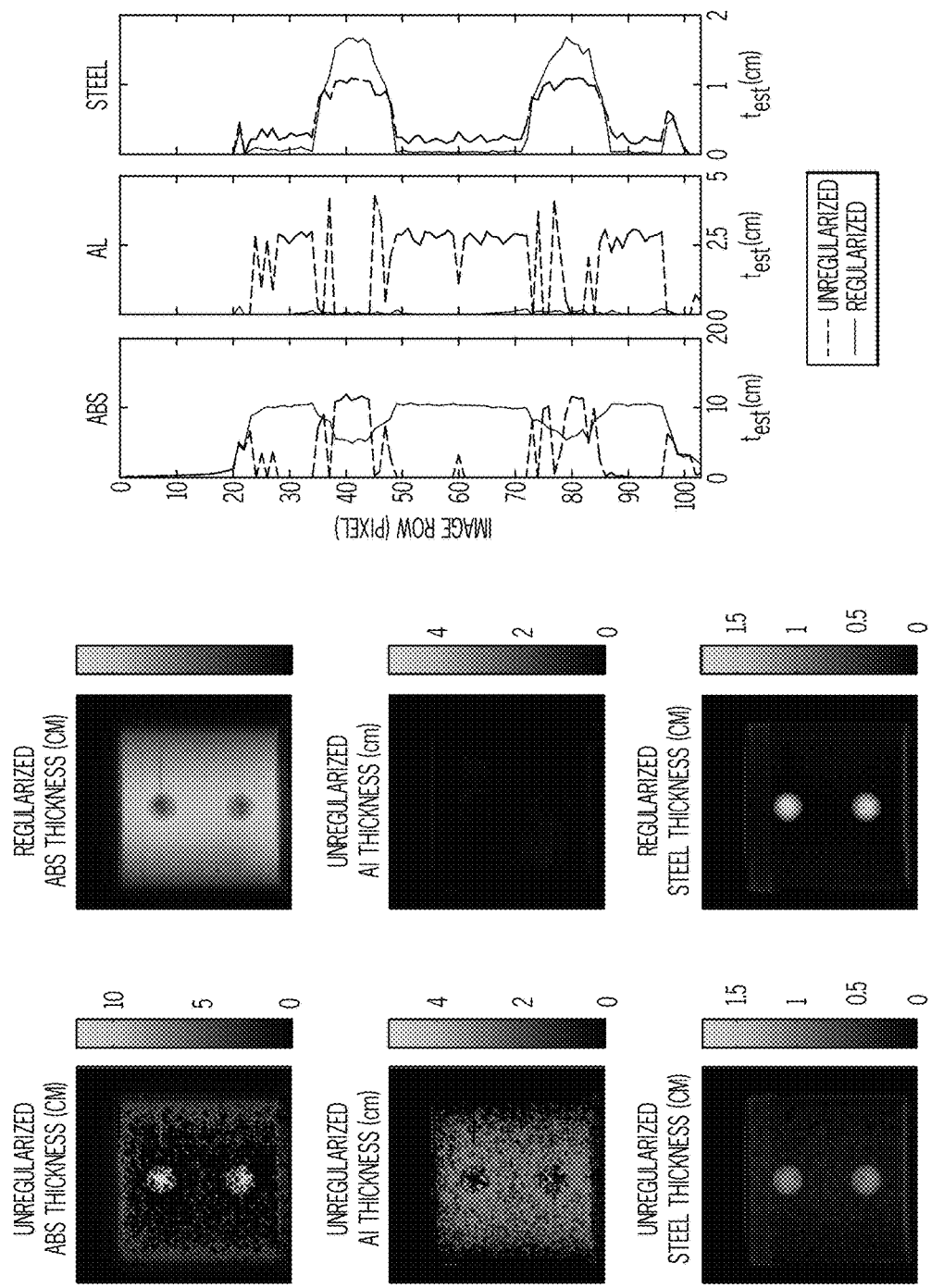
FIG. 7A illustrates the material estimations from the algorithm without and with regularization with experimental X-ray data containing the 150, 250, 300 and 450 keV endpoint scans in accordance with an embodiment of the present invention.
FIG. 7B illustrates the removal of noise and the near complete removal of the aluminum estimation with the addition of regularization in accordance with an embodiment of the present invention.

The principles of the present invention provide a means for effectively detecting and quantifying materials, including nuclear materials, utilizing X-ray radiography utilizing an inverse algorithm with adaptive regularization as discussed further below in connection with FIGS. 1-4, 5A-5C, 6A-6B and 7A-7B. FIG. 1 is an x-ray scanning system for detecting materials, such as illicit materials (e.g., nuclear materials, such as plutonium) in a container (e.g., storage containers). FIG. 2 illustrates a hardware configuration of the material detection system. FIG. 3 is a flowchart of a method for detecting a presence and an amount of a material (e.g., nuclear material) in a container utilizing an inverse algorithm with adaptive regularization. FIG. 4 is a flowchart of a method of the sub-steps of steps 304-307 of FIG. 3. FIG. 5A illustrates the radiographic image of the original X-ray transmission image of the scale AT400R model for the 300 keV endpoint energy. FIG. 5B illustrates the flat field image without the inspected object present. FIG. 5C illustrates the result of the division of the transmission image by the flat field image after the dark image is subtracted from both. FIG. 6A illustrates the scale-model object used in the inspections. FIG. 6B shows the experimental setup and detector. FIG. 7A illustrates the material estimations from the algorithm without and with regularization with experimental X-ray data containing the 150, 250, 300 and 450 keV endpoint scans. FIG. 7B illustrates the removal of noise with the addition of regularization with the estimation of aluminum being nearly completely removed.

Referring now to the Figures in detail, FIG. 1 is an X-ray scanning system 100 for detecting the presence and an amount of a material (e.g., illicit materials, such as nuclear materials) in a container (e.g., cargo, storage containers, luggage) in accordance with an embodiment of the present invention. X-ray scanning system 100 includes an X-ray source 101 (e.g., tungsten-anode x-ray tube) for emitting an x-ray beam of energy that is adapted to illuminate an object 102 (e.g., nuclear material) within a container 103 (e.g., storage container). The X-ray source may or may not emit multiple X-ray spectra in the inspection. In one embodiment, penetrating X-ray radiation emanating from source 101 in primary beam 104 passes through a primary beam collimator 105, which restricts the x-ray flux to a fan beam 106. A "fan beam" refers to a beam that is substantially wider in a first transverse direction perpendicular to the beam direction than in a second transverse direction. Preferably, the beam is about 1 mm wide in its second transverse direction and is at least about 10 times wider in the first direction. Fan beam 106 impinges on object 102. While FIG. 1 illustrates the use of fan beam 106, the principles of the present invention are not limited to the use of a fan beam.

A portion of the flux in beam 106 is not attenuated and emerges from object 102 as transmitted beam 107, which strikes a detector array 108. Container 103 is transported through enclosure 109 by motion means, such as a conveyor system 110 of conventional design.

As further illustrated in FIG. 1, X-ray scanning system 100 includes a material detection system 111 connected to detector array 108, which may or may not be sensitive to X-ray energy. In one embodiment, detector array 108 includes a scintillator (not shown) that converts the X-ray photons in transmitted beam 107 to lower energy photons in the visible spectrum. Contiguous with the scintillator is an image photo detector array (not shown) which converts the light photons into electrical signals. An electrical pattern is formed based on these electrical signals. Material detection system 111 then produces a digital image (radiograph) from the electrical pattern. In another embodiment, detector array 108 (e.g., a semiconductor-type detector) can determine incident X-ray energy.

Material detection system 111 is configured to utilize an inverse algorithm with adaptive regularization on the electrical pattern used to form the radiograph to detect the presence and an amount of a material, including illicit materials (e.g., nuclear materials, such as plutonium) in container 103 as discussed further below. A description of the hardware configuration of material detection system 111 is provided below in connection with FIG. 2.

Referring now to FIG. 2, FIG. 2 illustrates a hardware configuration of material detection system 111 (FIG. 1) which is representative of a hardware environment for practicing the present invention. Referring to FIG. 2, material detection system 111 has a processor 201 coupled to various other components by system bus 202. An operating system 203 runs on processor 201 and provides control and coordinates the functions of the various components of FIG. 2. An application 204 in accordance with the principles of the present invention runs in conjunction with operating system 203 and provides calls to operating system 203 where the calls implement the various functions or services to be performed by application 204. Application 204 may include, for example, an application for detecting the presence or an amount of a material (e.g., nuclear materials, such as plutonium) in container 103 utilizing an inverse algorithm with adaptive regularization as discussed below in association with FIGS. 3-4, 5A-5C, 6A-6B and 7A-7B.

Referring again to FIG. 2, read-only memory ("ROM") 205 is coupled to system bus 202 and includes a basic input/output system ("BIOS") that controls certain basic functions of material detection system 111. Random access memory ("RAM") 206 and disk adapter 207 are also coupled to system bus 202. It should be noted that software components including operating system 203 and application 204 may be loaded into RAM 206, which may be material detection system's 111 main memory for execution. Disk adapter 207 may be an integrated drive electronics ("IDE") adapter that communicates with a disk unit 208, e.g., disk drive. It is noted that the program for detecting the presence or an amount of a material, including illicit materials (e.g., nuclear materials, such as plutonium) in container 103 utilizing an inverse algorithm with adaptive regularization, as discussed below in association with FIGS. 3-4, 5A-5C, 6A-6B and 7A-7B, may reside in disk unit 208 or in application 204.

Material detection system 111 may further include a communications adapter 209 coupled to bus 202. Communications adapter 209 interconnects bus 202 with an outside network thereby enabling material detection system 111 to communicate with other such systems.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As discussed above, the principles of the present invention provide a means for effectively and automatically detecting and quantifying materials (e.g., nuclear material) in a container utilizing X-ray radiography with an inverse algorithm with adaptive regularization. A flowchart of a method for detecting the presence and an amount of a material, including illicit materials, in a container utilizing an inverse algorithm with adaptive regularization is discussed below in connection with FIG. 3.

FIG. 3 is a flowchart of a method 300 for detecting the presence and an amount of a material, including illicit materials (e.g., nuclear materials) in a container (e.g., container 103 of FIG. 1) utilizing an inverse algorithm with adaptive regularization in accordance with an embodiment of the present invention.

Referring to FIG. 3, in conjunction with FIGS. 1-2, in step 301, x-ray source 101 emits x-ray radiation towards object 102 in container 103, either as a single spectrum or multiple spectra.

In step 302, primary beam collimator 105 limits the radiation emanating from x-ray source 101 to a primary fan beam 106 which impinges on object 102 in container 103.

In step 303, detector array 108 detects transmitted beam 107, which is a portion of the flux in beam 106 that is not attenuated by object 102 and emerges from object 102. Detector array 108 may or may not be able to detect incident X-ray energy.

In step 304, material detection system 111 generates a radiograph from transmitted X-ray beam 107 at detector array 108, such as the electrical pattern formed from converting the light photons of the transmitted beam 107 into electrical signals.

In step 305, material detection system 111 applies an inverse algorithm to the data collected at detector array 108 varying the composition of object 102 until the predicted image matches the measured image.

In step 306, material detection system 111 implements regularization to provide details regarding density to enhance ability to discriminate possible materials (e.g., plutonium, uranium) that object 102 could comprise.

In step 307, material detection system 111 estimates the material composition (e.g., thickness of 1.9 cm) of object 102 (e.g., steel). If the purpose of the inspection system is detection of illicit materials, steps 308-310 may be utilized. Otherwise, they may be omitted from the process.

In step 308, a determination is made by material detection system 111 as whether the estimated material composition of object 102 (e.g., plutonium thickness of 0.3 cm) exceeds a threshold (e.g., threshold of 0.1 cm for plutonium).

If the estimated material composition of object 102 exceeds a threshold, then, in step 309, material detection system 111 issues a warning (e.g., via e-mail, text message, audio alert, etc.) regarding the material composition of object 102 exceeding a threshold. In this manner, material detection system 111 can inform the user of detecting a material, such as an illicit material (e.g., nuclear material) that exceeds a designated amount. In one embodiment, the threshold may be designated to be any amount of the material. Hence, if any amount of the material is detected, then material detection system 111 will issue a warning indicating detection of that material.

If the estimated material composition of material 102 does not exceed the threshold, then, in step 310, material detection system 111 does not issue a warning.

A detailed description of steps 304, 305, 306 and 307 is provided below in connection with FIG. 4.

FIG. 4 is a flowchart of a method of the sub-steps of steps 304-307 of FIG. 3 in accordance with an embodiment of the present invention.

Referring to FIG. 4, in conjunction with FIGS. 1-3, in step 401, material detection system 111 obtains the detector response (response at detector array 108) from detector array 108.

In step 402, material detection system 111 generates a radiograph from the detector response.

It has been previously shown that energy-discriminating X-ray detectors can be used to differentiate between high density and nuclear materials in small, layered objects (e.g., baggage). It is shown herein that this approach can be adapted for use with multiple X-ray spectra and standard detectors. The algorithm is tested against both simulated and experimental data. The discussion herein is focused on experimentally acquired data using a mid-energy X-ray scanner. These types of inspections may not be possible with energy discriminating detectors since they are currently limited to low-energy X-rays.

The interaction of an X-ray beam with an object comprised of K materials can be described using a modified form of Beer's law:

$$\Phi_\ell(\vec{p}, E) = \Phi_{0,\ell}(E) \exp\left[-\sum_{k=1}^{K} \mu_k(E)\rho_k\right] + \Phi_{scatter}(E) \quad (1)$$

Here, $\Phi_\ell$ [X-rays·cm$^{-2}$·keV$^{-1}$] is the X-ray energy-dependent fluence incident on the detector plane for inspection energy l, $\Phi_{0,l}$ [X-rays·cm$^{-2}$·keV$^{-1}$] is the incident fluence, $\mu_k$ [cm$^{2.1}$] is the energy dependent mass attenuation coefficient for material k, $\rho_k$ [g·cm$^{-2}$] is its areal density, and $\Phi_{scatter}$ [X-rays·cm$^{-2}$·keV$^{-1}$] is the fluence from X-rays that are scattered onto the image plane.

The subsequent detector response can be given by:

$$d(\vec{p}, E_\ell) = \int_E S(E)\Phi_\ell(\vec{p}, E)dE \quad (2)$$

Here S [gray-level·X-ray$^{-1}$·keV$^{-1}$·pixel$^{-1}$] is the system response, which relates the X-ray flux on the detector to the subsequent observed radiograph.

In systems utilizing a varying input spectrum (i.e., detector array 108 does not consist of energy resolving detectors), then the following steps, steps 403-404, are implemented. Otherwise, if the system utilizes energy resolving detectors (i.e., detector array 108 consists of energy resolving detectors), then steps 403 and 404 need not be implemented.

In step 403, material detection system 111 subtracts the dark current image from the object image (X-ray transmission image of object 102) and the flat field image (X-ray transmission image without inspected object present).

In step 404, material detection system 111 divides the X-ray radiograph (X-ray radiograph obtained from data collected at detector array 108) by a flat-field image and applies a convolution operator matrix which models the finite spatial resolution of the imaging system.

It is common in the processing of X-ray radiographs to divide by a flat-field image, i.e., an image without the object being inspected, and apply a convolution operator, which emulates the finite spatial resolution of the imaging system. This removes nonuniformities in the data due to variable detector response and source strength:

$$d'(\vec{p}, E_\ell) = C \frac{\int_E S(E)\Phi_\ell(\vec{p}, E)dE}{\int_E S(E)\Phi_{0,\ell}(\vec{p}, E)dE} \quad (3)$$

Here C is a multiplicative 2-D convolution matrix which models the finite spatial resolution of the imaging system. The dark current image for both the object and flat field images are also subtracted before division. The results of this processing are shown in FIGS. 5A-5C. FIG. 5A illustrates the radiographic image of the original X-ray transmission image of the scale AT400R model for the 300 keV endpoint energy in accordance with an embodiment of the present invention. FIG. 5B illustrates the flat field image without the inspected object present in accordance with an embodiment of the present invention. FIG. 5C illustrates the result of the division of the transmission image by the flat field image after the dark image is subtracted from both in accordance with an embodiment of the present invention. The scales are given in gray-level (ADU) (Analog-to-Digital Unit).

In step 405, material detection system 111 selects a set of materials of interest (e.g., plutonium, steel, polyethylene) to determine if object 102 in container 103 corresponds to one of these materials of interest. In connection with selecting the set of materials of interest, the attenuation coefficients for these materials of interest is obtained as discussed further below.

In step 406, material detection system 111 obtains the estimated areal densities for each of the selected materials of interest by minimizing an objective function (inverse algorithm) with respect to the areal densities for each selected material of interest.

The material composition of an object can then be estimated by minimizing an objective function with respect to a set of suspected material areal densities:

$$F(\vec{\rho}) = \|\vec{d}'(\vec{\rho}) - \vec{d}'_{obs}\|^2 \quad (4)$$

Here, $\vec{d}'(\vec{\rho})$ is a vector containing modeled signals at each pixel of the radiograph and $\vec{d}_{obs}$ is a vector containing the observed signals at each pixel for each scan. The combination and quantity of the materials at each pixel are varied until a minimum for F is found. The minimization of Eq. (4) represents a classic inverse problem, where Eqs. (1-3) constitute the "forward" part of the problem.

In step 407, material detection system 111 implements regularization to the objective function to improve optimization results by adding a constraint to the objective function, where the constraint penalizes the objective function as sums of differences in material compositions for each selected material of interest in column and row dimensions at each pixel of the radiograph.

In practice, it can be difficult to obtain accurate results with Eq. (4) if the radiographic signal contains noise. The optimization can be improved if addition information can be added to the inverse problem. In one embodiment, information on the path length of X-rays through the object, obtained using computed tomography, can be used. Where this information is absent, regularization (the process of introducing additional information in order to solve an ill-posed problem) can be used to improve optimization results in these situations, and amounts to adding a constraint or additional information to the optimization problem. In one embodiment, this would take the form:

$$F(\vec{\rho}) = \frac{1}{2}\|\vec{d}'(\vec{\rho}) - \vec{d}'_{obs}\|^2 + \alpha \Sigma \sqrt{(D_i\vec{\rho})^2 + (D_j\vec{\rho})^2 + \beta} \quad (5)$$

Here the left-hand term in F is the least-squares misfit and the right-hand term is the total variation regularization, which includes a weighting term α that varies the strength of the regularization. In one embodiment, the total variation term added to the objective function sums the differences in the material composition for each of the materials of interest in column and row dimensions at each pixel of the radiograph. Backwards finite difference matrix operators in the row and column image dimension are given by $D_i$ and $D_j$, respectively. The term β ensures that the function is differentiable so that analytical first and second derivatives can be found for optimization. In one embodiment, the value for α was selected adaptively within the optimization algorithm using the unbiased predictive risk estimator (UPRE) method explained below. The minimum of Eq. (4) is found using the Gauss-Newton algorithm, with the application of a non-negativity constraint using the projected gradient, reduced Hessian algorithm.

In connection with the UPRE method, this method seeks a statistical estimator of the predictive risk:

$$\frac{1}{n}\|\vec{\rho}_\alpha\|^2 = \frac{1}{n}\left(\vec{d}(\vec{\rho}_\alpha) - \vec{d}(\vec{\rho}_{true})\right)\|^2 \quad (6)$$

where $\vec{\rho}_\alpha$ is the regularized solution vector from the algorithm, $\vec{\rho}_{true}$ is the true material composition, and n is the number of elements in $\vec{\rho}_\alpha$. Since $\vec{\rho}_{true}$ is not available to directly calculate the predictive risk, an estimator, the UPRE, is given:

$$U(\alpha) = E\left(\frac{1}{n}\|\vec{\rho}_\alpha\|^2\right) = \frac{1}{n}\|\vec{r}_\alpha\|^2 + \frac{2\sigma^2}{n}\text{trace}(A_\alpha) - \sigma^2 \quad (7)$$

where $$\vec{r}_\alpha = \frac{\vec{d}(\vec{\rho}_\alpha) - \vec{d}_{obs}}{\sqrt{\vec{d}(\vec{\rho}_\alpha)}} \text{ and}$$

$$A_\alpha = K(K^T K + \alpha L)^{-1} K^T.$$

Here $\vec{r}\alpha$ is the regularized residual vector, $\sigma^2$ is the scalar variance of the noise in the data, and $A_\alpha$, is called the influence matrix, which depends on a linear forward problem operator matrix K and a penalty operator L. The value for $\sigma^2$ is taken to be 1 since the expected variance of the normalized residual is 1. This is because the expected variance of a Poisson random variable, x, is x. The optimal value of a according to this method is that which minimizes Eq. (7). Since neither K nor L can be directly computed from the problem, they both are approximated. The forward problem operator K was approximated with the Jacobian of the forward problem at the regularized solution, $J(\vec{\rho}_\alpha)$. The penalty operator used was a representation of the total variation regularization term $$L = \sqrt{(D_i)^2 + (D_j)^2 + \beta}. \quad (8)$$

This selection of the penalty operator was found to perform better than other linearizations tested, including the Jacobian and the Hessian of the regularization term.

Referring again to Eq. (5), the data vector d' in Eq. (5) is column-stacked and includes the modeled data for each image pixel and endpoint, and, similarly, the ρ includes all material areal densities for each material at each image pixel. The term β ensures that F is differentiable for all possible sets of ρ and, in one embodiment, is set to 1. In the absence of information on the path length of X-rays through an object, the regularization term is required because the problem is considered ill-posed and solutions without this term are typically unstable. The reason for the ill-posedness is the limited uniqueness in the bases for discrimination, here the material attenuation coefficients, μ. Additionally, common Bremsstrahlung X-ray sources were used, which have large overlapping regions in energy.

Newton-type algorithms are used to optimize Eq. (5). Here F is optimized iteratively by approximating it as locally quadratic at each iteration and minimizing Eq. (5) accordingly. In order to use this method, the first derivative (gradient) and second derivative (Hessian) of F, or an approximation thereof, are found at each Newton iteration. The misfit term is optimized using the Gauss-Newton algorithm, which approximates the second derivative with the Jacobian matrix. This saves computation time since a full second derivative matrix (the Hessian) does not have to be calculated at each iteration. This approximation was found to perform comparably to that when the full analytical Hessian matrix was used. In contrast, for the regularization term, the full analytical Hessian is calculated at each iteration, which is computationally inexpensive due to the sparse operator matrices, $D_i$ and $D_j$, used in this term. A non-negativity constraint is put on the solution by using the projected gradient, reduced Hessian algorithm.

An initial guess for ρ is set in the algorithm to the zero vector, $\vec{0}$, and a stopping criterion for the Newton iterations is set to be when the maximum change in any value of ρ is less than a user-defined tolerance. In one embodiment, the algorithm is implemented in Matlab®.

Experimental Setup and Radiography

In one embodiment, the Bremsstrahlung X-ray source used in the experiment was a 450 keV Comet MXR-451/26. It has a tungsten target at a 30° takeoff angle with 5 mm integrated beryllium filtering, a variable source spot size of 2.5 mm or 5.5 mm, and is tunable from 100 to 450 keV with a maximum current of 4.9 A. The detector used was the PerkinElmer XRD-0822-AP, which has a 140 μm thick $Gd_2O_2S$:Tb (GOS) scintillator and a 1024×1024 pixel matrix of 200 μm pitch. The signal output is digitized to 16 bits and the readout electronics are shielded to reduce noise.

A ½ inch stainless steel filter was put on the source in order to harden the X-ray spectra to have greater transmission through dense objects relative to the unattenuated signal. The unfiltered source was found to be too heavily attenuated to accurately estimate the dense material thicknesses. Seven source spectra were used in the inspection with endpoints of {150, 200, 250, 300, 350, 400, 450} keV and corresponding currents of {1.0, 1.25, 1.7, 2.5, 3.4, 3.6, 5.0} mA. Variable exposure times were used for the various endpoint energies in order to best use the available dynamic range on the detector. Five second exposures were used for the 150 and 200 keV endpoint energies, a 2.5 second exposure for the 250 keV endpoint, and 2 second exposures for the endpoints of 300 keV and above. In order to reduce the variability from one exposure to the next, the image data used in the analysis was an average of 32 individual exposures, for a varied total exposure time depending on the endpoint of the spectra, from about 1 minute to 2.5 minutes. For data analysis, subsets of the data from the seven endpoints were used.

The object to be inspected was a scale-model of a nominal nuclear materials storage container. It is composed of two spherical steel spheres held in a plastic (ABS) cylinder which is placed in a steel can. The spheres put in the container were stainless steel 304 of 1.9 cm diameter. The plastic piece (ABS-P400, Stratasys) was made with a 3-D printer and had a diameter of 10.1 cm with cavities to hold the spheres. This object is shown in FIG. 6A, where FIG. 6A illustrates the scale-model object used in the inspections in accordance with an embodiment of the present invention. Furthermore, the experimental setup and detector is shown in FIG. 6B in accordance with an embodiment of the present invention.

Error Calculations

The root mean square error (RMSE) is used as a measure of goodness-of-fit of the material estimates from the algorithm to the ground-truth. Even though the ground-truth for the experimental data is not directly known, careful estimations have been made and these are used for the RMSE calculations for the experimental results.

Results

FIG. 7A illustrates the material estimations from the algorithm without and with regularization with experimental data acquisitions containing the 150, 250, 300 and 450 keV endpoint scans in accordance with an embodiment of the present invention. It is noted that the large noise in the unregularized estimation, especially between the ABS and aluminum estimations. FIG. 7B illustrates that much of this noise is removed with the addition of regularization, with the estimation of aluminum being nearly completely removed in accordance with an embodiment of the present invention. The steel thickness is still underestimated (the maximum should be 1.9 cm) likely because of the limited transmission through the greatest thickness of the steel sphere.

As illustrated in FIGS. 7A and 7B, the chosen basis material set is {steel, aluminum, ABS plastic}, consistent with the actual scale-model composition. The aluminum basis material is put in the basis set to emulate the three basis material reconstruction that could be accomplished with the simulated data. The regularization weighting factor $\alpha$ is set to $10^{-7}$ for all of the results in this section, and was found to perform well for all of the data considered. Qualitatively, the material estimations with regularization appear very good. The steel spheres are picked out with good contrast and even the profile of the steel can is visible in the steel estimation, indicating sub-millimeter precision with these methods. Even still, the maximum steel thickness at the steel spheres is underestimated by 0.38 cm. In contrast, the estimations without regularization are very noisy, especially in the ABS and Al results, and the steel sphere thickness is more significantly underestimated by 0.85 cm.

A comparison of the regularized results and the unregularized gives a good illustration of the utility of regularization in these types of problems. Regularization smooths the solution while also improving accuracy and shows significant utility for the noninvasive inspections used here. Though the results show an underestimate of the maximum steel thickness, this is expected due to: 1. the limited signal (X-ray flux through the middle of the steel spheres); and 2. that the optimization effectively involves a deconvolution and it is difficult to reconstruct the full spherical profile with such an operation. This effect would likely be mitigated with greater X-ray transmission (with a higher-energy scan) and/or a reduction in the scattered flux with an anti-scatter grid. Furthermore, accuracy in material estimations would likely be improved by utilizing X-ray scans of higher or lower energy, or by considering a material set with a wider range of atomic number, both of which would result in greater uniqueness of the attenuation coefficients.

TABLE 2

The root mean square error (RMSE) of the experimental estimated steel thicknesses compared to the actuals. The RMSE is calculated around the location of the steel spheres, not accounting for the steel can.

| Endpoint set (keV) | Reg. RMSE Steel (cm) | Unreg. RMSE Steel (cm) |
|---|---|---|
| 150, 250, 300, 450 | 0.30 | 0.50 |
| 350, 450 | 0.30 | 0.57 |

The principles of the present invention have shown that multi endpoint radiography can be used in conjunction with an inverse algorithm and regularization to determine the material composition of objects. Though the methods presented herein were demonstrated for quantification of materials in nominal material storage containers, the algorithms have potential to be used in inspection of cargo containers, semi-trucks, etc. However, in these cases the geometry is variable and can include any number of materials. Fortunately, the algorithm has shown utility when not all of the materials actually present in the object are included in the material basis set. Furthermore, the principles of the present invention can be equivalently applied to X-ray scans where the detector can determine to some extent the incident X-ray energy.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A method for automatically detecting or quantifying a presence of a material in a container, the method comprising:

generating a radiograph from a detector response at a detector array, wherein said detector array detects a transmitted beam which emerges from an object in a container, wherein said transmitted beam is a portion of a flux in an X-ray beam that is not attenuated by said object;

selecting a set of materials of interest used to determine if said object in said container corresponds to one or more of these materials of interest;

obtaining, by a processor, estimated areal densities for each of said selected set of materials of interest by minimizing an objective function with respect to said areal densities, or linear attenuation coefficients, for each of said selected set of materials of interest, wherein said objective function comprises a least-squares misfit of a vector containing observed signals at each pixel of said radiograph and a model of said radiography detector response, wherein said minimizing of said objective function occurs by varying a combination and a quantity for each of said selected set of materials of interest at each pixel of said radiograph model until a minimum of said objective function is found;

implementing adaptive regularization to said objective function to improve optimization results by adding a constraint to said objective function, wherein said constraint penalizes said objective function as sums of differences in material compositions for each of said selected set of materials of interest in column and row dimensions at each pixel of said radiograph; and estimating a material composition of said object by minimizing said objective function with respect to said estimated areal densities for said selected set of materials of interest.

2. The method as recited in claim 1, wherein said objective function with said regularization is:

$$F(\vec{\rho})=\tfrac{1}{2}\|\vec{d}\,'(\vec{\rho})-\vec{d}\,'_{obs}\|^2+\alpha\Sigma\sqrt{(D_i\vec{\rho})^2+(D_j\vec{\rho})^2}+\beta$$

where $F(\vec{\rho})$ is a vector of said material composition of said object, $\vec{d}'(\vec{\rho})$ is a vector containing modeled signals at each pixel of said radiograph, $\vec{d}_{obs}$, is a vector containing said observed signals at each pixel of said radiograph, $\alpha$ is a weighting term, and $\beta$ is a term that ensures that the function is differentiable so that analytical first and second derivatives are found for optimization.

3. The method as recited in claim 2, wherein said $\alpha$ is determined adaptively.

4. The method as recited in claim 1 further comprising: issuing a warning in response to said estimated material composition of said object exceeding a threshold.

5. The method as recited in claim 1, wherein said object contains an illicit material or material of interest.

6. The method as recited in claim 1, wherein said container is one of the following: cargo, a storage container, luggage, equipment, and componentry in a facility processing or handling the materials of interest.

7. The method as recited in claim 1 further comprising: subtracting a dark current image from both an image of said object and a flat field image; and
dividing said radiograph by said flat field image and/or normalizing said radiograph using a function of said flat field image and applying a convolution operator matrix which models a finite spatial resolution of an imaging system.

8. The method as recited in claim 1 further comprising: emitting x-ray radiation from an x-ray source; and
limiting radiation emanating from said x-ray source to a primary fan beam via a primary beam collimator which impinges on said object in said container.

9. A computer program product for detecting a presence of a material in a container, the computer program product comprising a computer readable storage medium having program code embodied therewith, the program code comprising the programming instructions for:
generating a radiograph from a detector response at a detector array, wherein said detector array detects a transmitted beam which emerges from an object in a container, wherein said transmitted beam is a portion of a flux in an X-ray beam that is not attenuated by said object;
selecting a set of materials of interest used to determine if said object in said container corresponds to one or more of these materials of interest;
obtaining estimated areal densities for each of said selected set of materials of interest by minimizing an objective function with respect to said areal densities, or linear attenuation coefficients, for each of said selected set of materials of interest, wherein said objective function comprises a least-squares misfit of a vector containing observed signals at each pixel of said radiograph and a model of said radiography detector response, wherein said minimizing of said objective function occurs by varying a combination and a quantity for each of said selected set of materials of interest at each pixel of said radiograph model until a minimum of said objective function is found;
implementing adaptive regularization to said objective function to improve optimization results by adding a constraint to said objective function, wherein said constraint penalizes said objective function as sums of differences in material compositions for each of said selected set of materials of interest in column and row dimensions at each pixel of said radiograph; and
estimating a material composition of said object by minimizing said objective function with respect to said estimated areal densities for said selected set of materials of interest.

10. The computer program product as recited in claim 9, wherein said objective function with said regularization is:

$$F(\vec{\rho})=\tfrac{1}{2}\|\vec{d}\,'(\vec{\rho})-\vec{d}\,'_{obs}\|^2+\alpha\Sigma\sqrt{(D_i\vec{\rho})^2+(D_j\vec{\rho})^2}+\beta$$

where $F(\vec{\rho})$ is a vector of said material composition of said object, $\vec{d}'(\vec{\rho})$ is a vector containing modeled signals at each pixel of said radiograph, $\vec{d}_{obs}$ is a vector containing said observed signals at each pixel of said radiograph, $\alpha$ is a weighting term, and $\beta$ is a term that ensures that the function is differentiable so that analytical first and second derivatives are found for optimization.

11. The computer program product as recited in claim 10, wherein said $\alpha$ is determined adaptively.

12. The computer program product as recited in claim 9, wherein the program code further comprises the programming instructions for:
issuing a warning in response to said estimated material composition of said object exceeding a threshold.

13. The computer program product as recited in claim 9, wherein said object contains an illicit material or material of interest.

14. The computer program product as recited in claim 9, wherein said container is one of the following: cargo, a storage container, luggage, equipment, and componentry in a facility processing or handling the materials of interest.

15. The computer program product as recited in claim 9, wherein the program code further comprises the programming instructions for:
subtracting a dark current image from both an image of said object and a flat field image; and
dividing said radiograph by said flat field image and/or normalizing said radiograph using a function of said flat field image and applying a convolution operator matrix which models a finite spatial resolution of an imaging system.

16. A system, comprising:
a memory unit for storing a computer program for detecting a presence of a material in a container; and
a processor coupled to the memory unit, wherein the processor is configured to execute the program instructions of the computer program comprising:
generating a radiograph from a detector response at a detector array, wherein said detector array detects a transmitted beam which emerges from an object in a container, wherein said transmitted beam is a portion of a flux in an X-ray beam that is not attenuated by said object;
selecting a set of materials of interest used to determine if said object in said container corresponds to one or more of these materials of interest;
obtaining estimated areal densities for each of said selected set of materials of interest by minimizing an objective function with respect to said areal densities, or linear attenuation coefficients, for each of said selected set of materials of interest, wherein said objective function comprises a least-squares misfit of a vector containing observed signals at each pixel of said radiograph and a model of said radiography detector response, wherein said minimizing of said objective function occurs by varying a combination and a quantity for each of said selected set of materials of interest at each pixel of said radiograph model until a minimum of said objective function is found;

implementing adaptive regularization to said objective function to improve optimization results by adding a constraint to said objective function, wherein said constraint penalizes said objective function as sums of differences in material compositions for each of said selected set of materials of interest in column and row dimensions at each pixel of said radiograph; and estimating a material composition of said object by minimizing said objective function with respect to said estimated areal densities for said selected set of materials of interest.

17. The system as recited in claim 16, wherein said objective function with said regularization is:

$$F(\vec{\rho}) = \frac{1}{2}\|\vec{d}\,'(\vec{\rho}) - \vec{d}\,'_{obs}\|^2 + \alpha \Sigma \sqrt{(D_i\vec{\rho})^2 + (D_j\vec{\rho})^2} + \beta$$

where $F(\vec{\rho})$ is a vector of said material composition of said object, $\vec{d}'(\vec{\rho})$ is a vector containing modeled signals at each pixel of said radiograph, $\vec{d}_{obs}$ is a vector containing said observed signals at each pixel of said radiograph, $\alpha$ is a weighting term, and $\beta$ is a term that ensures that the function is differentiable so that analytical first and second derivatives are found for optimization.

18. The system as recited in claim 17, wherein said $\alpha$ is determined adaptively.

19. The system as recited in claim 16, wherein the program instructions of the computer program further comprise:

issuing a warning in response to said estimated material composition of said object exceeding a threshold.

20. The system as recited in claim 16, wherein said object contains an illicit material or material of interest.

21. The system as recited in claim 16, wherein said container is one of the following: cargo, a storage container, luggage, equipment, and componentry in a facility processing or handling the materials of interest.

22. The system as recited in claim 16, wherein the program instructions of the computer program further comprise:

subtracting a dark current image from both an image of said object and a flat field image; and dividing said radiograph by said flat field image and/or normalizing said radiograph using a function of said flat field image and applying a convolution operator matrix which models a finite spatial resolution of an imaging system.

* * * * *